United States Patent
Kubein-Meesenburg et al.

(10) Patent No.: US 6,902,582 B2
(45) Date of Patent: Jun. 7, 2005

(54) ARTIFICIAL JOINT PARTICULARLY SUITABLE FOR USE AS AN ENDOPROSTHESIS FOR A HUMAN KNEE JOINT

(75) Inventors: Dietmar Kubein-Meesenburg, Goettingen (DE); Hans Naegerl, Gleichen (DE); Peter Adam, Dachau (DE); Joachim Theusner, Munich (DE)

(73) Assignee: HJS Gelenk System GmbH, Munich (DE)

( * ) Notice: Subject to any disclaimer, the term of this patent is extended or adjusted under 35 U.S.C. 154(b) by 0 days.

(21) Appl. No.: 10/616,230

(22) Filed: Jul. 10, 2003

(65) Prior Publication Data

US 2004/0122522 A1 Jun. 24, 2004

(30) Foreign Application Priority Data

Jul. 11, 2002 (DE) ........................................ 102 31 538

(51) Int. Cl.[7] ................................................. A61F 2/38
(52) U.S. Cl. ................................ 623/20.31; 623/20.21; 623/20.14
(58) Field of Search ............................. 623/20.14–20.36

(56) References Cited

U.S. PATENT DOCUMENTS 5,871,539 A * 2/1999 Pappas .................... 623/20.31

6,235,060 B1 * 5/2001 Kubein-Meesenburg et al. 623/20.31

FOREIGN PATENT DOCUMENTS

| DE | 3908958 | 9/1990 |
|---|---|---|
| DE | 19521597 | 12/1996 |
| DE | 19646891 | 5/1998 |
| EP | 0600806 | 6/1994 |
| EP | 0734700 | 10/1996 |

* cited by examiner

*Primary Examiner*—David J. Isabella
(74) *Attorney, Agent, or Firm*—Crowell & Moring LLP

(57) ABSTRACT

An artificial joint (1) suitable for use as an endoprosthesis for a human knee joint, having a first joint compartment (2) formed by a first condyle (3) and a first socket (4) and a second joint compartment (5) formed by a second condyle (6) and a second socket (7). The contact surfaces (C) of the respective joint compartments (2, 5) are offset in the main functional plane. To further improve the characteristics of the artificial joint (1), the contact surfaces (C) of the two joint compartments (2, 5) are sloped as a function of the flexion angle such that the surface normals (8, 9) of the contact surfaces (C) have a common point of intersection at every flexion angle. This arrangement of the contact surfaces (C) achieves self-stabilization of the joint (1) both when a rotary motion or torsion and when lateral forces are introduced.

5 Claims, 1 Drawing Sheet

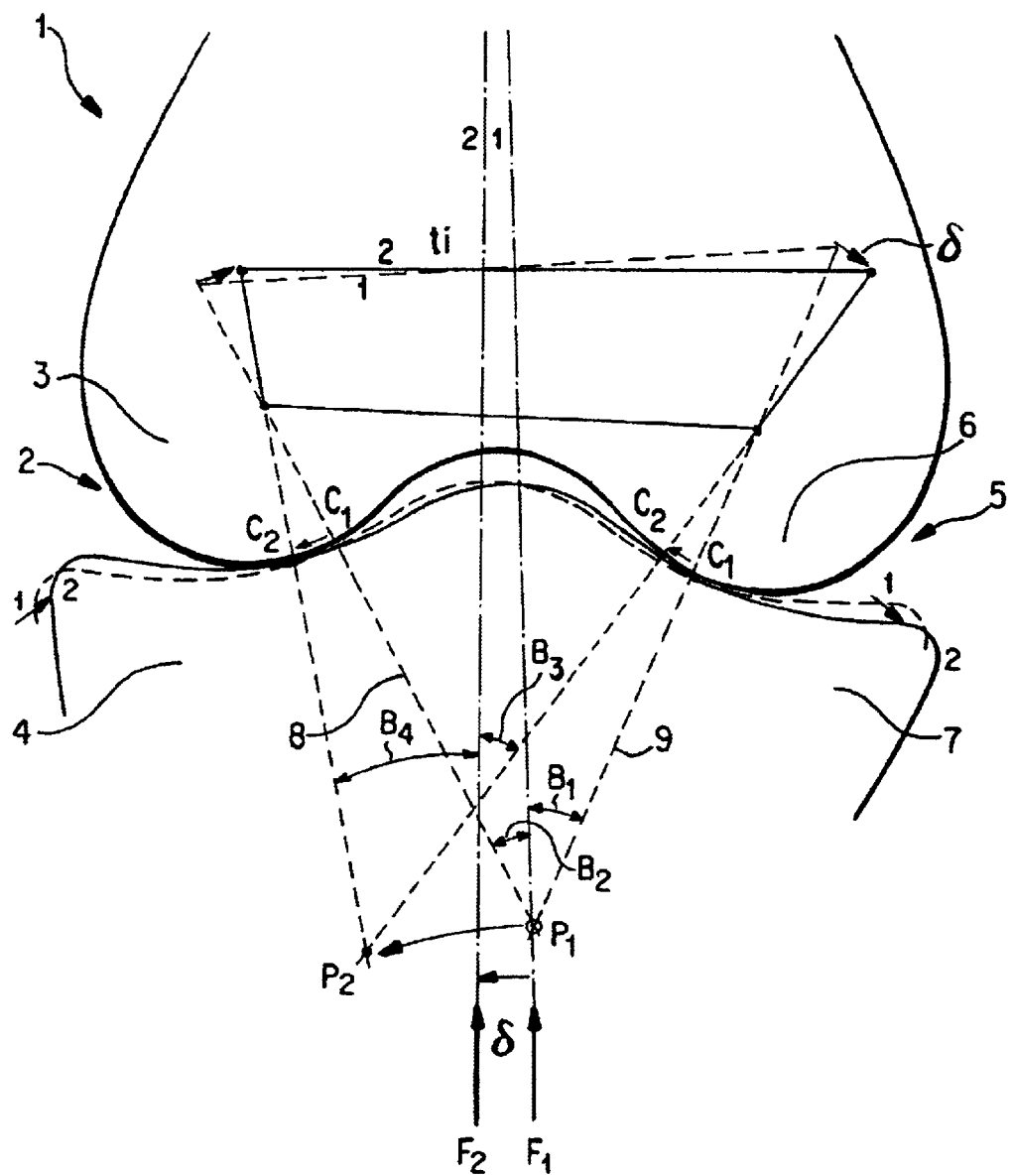

ARTIFICIAL JOINT PARTICULARLY SUITABLE FOR USE AS AN ENDOPROSTHESIS FOR A HUMAN KNEE JOINT

BACKGROUND OF THE INVENTION

This invention relates to an artificial joint intended, in particular, as an endoprosthesis for the human knee joint, comprising a first joint compartment formed by a first condyle and a first socket and a second joint compartment formed by a second condyle and a second socket. Contact surfaces of the respective joint compartments are offset in the main functional plane.

Published German patent application no. DE 39 08 958 A1 discloses an artificial joint intended to replace a human joint, which is made of two joint components with mobile functional surfaces. The curvature relationships of the functional surfaces having a circular cross-sectional contour are mutually convex-convex, convex-concave or concave-concave, and the joint geometry is determined by a joint chain with two joint axes (dimeric joint chain), which pass through the centers of rotation of the functional surfaces. The joint surfaces are spherical to enable the joint to move with five degrees of freedom.

Published European patent application no. EP 734,700 also discloses an artificial joint in which the joint geometry of the functional surfaces relative to one another is determined by a joint chain with two joint axes in each of the two planes. The joint axes pass through the centers of rotation of the functional surfaces with the radii of the respectively associated cross-sectional contours. A femur-side, i.e., a condyle-side, connection of the center points of the condyles corresponds to a frame and a tibia-side, i.e., a socket-side, connection of the center points of the sockets corresponds to a coupling of a four-bar linkage having the four axes. This makes it possible, in particular, in the flexion area of the joint between 0 and 30°, to obtain a high rolling component in the contact of the joint surfaces. The contact surfaces initially move in posterior direction relative to the socket. With further flexion, a sliding movement occurs without any shifting of the contact surface. As a result, the condyle cannot roll out of the socket.

SUMMARY OF THE INVENTION

It is the object of the invention to provide an artificial joint with improved properties.

A further object of the invention is to provide an artificial knee joint in which the motion sequences are improved in a way clearly noticeable to the patient.

Yet another object of the invention is to provide an artificial knee joint which approaches the natural sequence of motion of a: natural knee joint.

These and other objects are achieved in accordance with the present invention by providing an artificial joint comprising a first joint compartment formed by a first condyle and a first socket and a second joint compartment formed by a second condyle and a second socket, wherein two contact surfaces of the respective joint compartments are offset in a main functional plane, and wherein the contact surfaces of the two joint compartments are sloped as a function of the knee joint flexion angle such that surface normals of the contact surfaces have a common point of intersection at each flexion angle.

In accordance with a preferred aspect of the invention, the artificial joint is an endoprothesis for a human knee joint.

Further advantageous aspects and embodiments of the invention are set forth hereinafter.

Thus, according to the invention, an artificial joint is provided in which the contact surfaces of the two joint compartments are sloped as a function of the flexion angle, such that the surface normals of the contact surfaces have a common point of intersection at each flexion angle. The invention is based on the idea that a resultant force, particularly a torque, due to the ground reaction force at the different flexion angles, can be optimally avoided by mutually adjusting the contact surfaces in such a way that the effective lines of the forces introduced at the contact surfaces intersect. To this end, the contact surfaces are sloped such that the surface normals intersect in space.

This arrangement of the contact surfaces thus causes the joint to self-stabilize when a rotational motion or torsion about the tibia associated with the socket is introduced. Furthermore, the artificial joint is also adapted to balance the introduction of lateral forces and bring about the desired stabilization. This provides a noticeable improvement in the motion sequence for the patient. Due to the convex and concave shape of the condyles and the sockets, respectively, a change in the flexion angle causes a change in the angular position of the resultant contact surfaces.

In a particularly advantageous embodiment of the invention, the contact surfaces have a slope ascending to the center of the joint. As a result, any particles removed from the contact surfaces or any other abrasions are laterally discharged and thus do not interfere with the functioning of the joint.

In a particularly advantageous refinement of the invention, the contact surfaces on both sides of a convex curvature dividing the sockets of the first and the second joint compartment are arranged at a junction to a concave shape. As a result, even the introduction of reaction forces in a direction divergent from the main functional plane causes a change in the corresponding slope of the contact surfaces and thereby a restoring force counteracting the undesirable deflection and based on the ground reaction force, which leads to a reliable stabilization of the joint.

It has proven to be particularly practical if the surface normals of the two contact surfaces form an angle of maximum 40° relative to the effective direction of the resultant joint force loading the joint. This slope of the contact surfaces in view of the motion sequence makes possible the desired stabilization of the joint on the one hand and at the same time also allows a displacement motion, especially when external forces are introduced abruptly.

According to a further especially promising embodiment, the contact surfaces each have a different slope angle relative to the two joint compartments and/or the flexion angle. This makes it possible to realize the self-stabilization advantage according to the invention even in a four-bar arrangement and thereby to utilize the advantageous effect of such an arrangement.

BRIEF DESCRIPTION OF THE DRAWING

It is understood, of course, that the invention is susceptible to various embodiments. To further illustrate the basic principle of the invention, it will be described in further detail hereinafter with reference to an illustrative preferred embodiment shown in the accompanying drawing FIGURE which is a schematic cross-section of an artificial joint according to the invention.

DETAILED DESCRIPTION OF A PREFERRED EMBODIMENT

In the drawing, a schematic cross-section taken perpendicularly to the main functional plane shows an artificial joint 1, with a first condyle 3 and a first socket 4 forming a first joint compartment 2 and a second condyle 6 and a second socket 7 forming a second joint compartment 5.

It may be seen that two contact surfaces C of the joint compartments 2, 5 are located on the slopes of the tibial contour associated with the sockets 4, 7 and on the femoral contour associated with the condyles 3, 6 on the insides. A laterally introduced relative motion of the sockets 4, 7 in relation to the condyles 3, 6 causes the contact surfaces C1 to shift to the contact surfaces C2 and thus to the associated surface normals 8, 9. Preferably, the angles between each contact surface normal and the direction of their respective resultant joint loading lines are a maximum of 40 degrees. In the figure, these angles are denoted $B_1$–$B_4$.

This motion corresponds to a rotation of the tibia associated with the joint sockets 4, 7 at an angle δ about a momentary axis of rotation P, which simultaneously with the motion migrates from the position P1 to P2. This motion is modeled by a four-bar joint derived from the central curvature points of the contours. The line ti is the distance of the tibial center point and is stationary in the tibial coordinate system, which is in motion. The line ti also rotates at the angle δ. The effective force line of the resultant joint force F, which is composed, in particular, of muscle and weight forces, also rotates at the angle δ because the tibial starting points of the muscle forces likewise rotate about P at an angle δ.

Since with a suitable slope of the joint surfaces in the contact surfaces, C2 or the momentary axis of rotation P migrates further outward than the effective force line, the joint force F, in the position P2, produces a torque relative to P, which counteracts the rotation at the angle δ. The arrangement of the contact surfaces C on the slopes of the joint surfaces and suitable inclinations of these surfaces make it possible to achieve a mechanically stable equilibrium relative to abduction/adduction. A corresponding stabilization is also achieved for axial rotation of the tibia about its longitudinal axis.

Because of the slope of the two contact surfaces C in the joint contacts of the joint surfaces corresponding to every possible flexion angle, the axial rotation causes a distancing, an "unscrewing" of femur and tibia. The compressive joint force F, however, counteracts this unscrewing and mechanically stabilizes the initial position. Since due to the functional four-bar joint, each flexion angle has a predefined specific position of the medial or lateral contact surfaces C1 and C2 in the main functional plane, the slopes of the tangent surfaces in these contact positions are structurally optimized such that the self-stabilization effect occurs in every joint position.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations within the scope of the appended claims and equivalents thereof.

What is claimed is:

1. An artificial joint for use as an endoprosthesis for a human knee joint, said artificial joint comprising a first joint compartment formed by a first condyle and a first socket and a second joint compartment formed by a second condyle and a second socket, wherein two contact surfaces of the respective joint compartments are offset in a main functional plane, and wherein the contact surfaces of the two joint compartments are formed in each case by a point contact and are arranged at an angle as a function of the knee joint flexion angle such that surface normals of the contact surfaces have a single common point of intersection at each flexion angle.

2. An artificial joint according to claim 1, wherein the contact surfaces have a slope which ascends to a center of the joint.

3. An artificial joint according to claim 1, wherein the contact surfaces on both sides of a convex curvature dividing the joint socket of the first and second joint compartments are arranged at the junction to a concave shape.

4. An artificial joint according to claim 1, wherein the surface normals of the two contact surfaces form an angle of at most 40° relative to the effective direction of a resultant joint force loading the joint.

5. An artificial joint according to claim 1, wherein the contact surfaces each have a different slope angle.

* * * * *